United States Patent
Chien

(10) Patent No.: US 10,143,203 B2
(45) Date of Patent: Dec. 4, 2018

(54) ANTIBACTERIAL SPECTACLE PART AND ANTIBACTERIAL TREATMENT METHOD

(71) Applicant: MiiCs & Partners (Shenzhen) Co., Ltd., Shenzhen (CN)

(72) Inventor: Hsiu-Wen Chien, New Taipei (TW)

(73) Assignee: MiiCs & Partners (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/483,006

(22) Filed: Apr. 10, 2017

(65) Prior Publication Data

US 2018/0228160 A1    Aug. 16, 2018

(30) Foreign Application Priority Data

Feb. 13, 2017 (CN) .......................... 2017 1 0077366

(51) Int. Cl.
| | |
|---|---|
| *A61L 31/10* | (2006.01) |
| *C09D 5/00* | (2006.01) |
| *C09D 187/00* | (2006.01) |
| *A01N 59/16* | (2006.01) |
| *A61L 12/08* | (2006.01) |
| *G02C 7/04* | (2006.01) |
| *A61L 12/14* | (2006.01) |

(52) U.S. Cl.
CPC ............ *A01N 59/16* (2013.01); *A61L 12/088* (2013.01); *A61L 12/147* (2013.01); *A61L 31/10* (2013.01); *C09D 5/00* (2013.01); *C09D 187/00* (2013.01); *G02C 7/04* (2013.01)

(58) Field of Classification Search
None
See application file for complete search history.

(56) References Cited

U.S. PATENT DOCUMENTS

| | | | |
|---|---|---|---|
| 2005/0287111 A1* | 12/2005 | Schlenoff | A61K 31/785 424/78.3 |
| 2007/0172661 A1* | 7/2007 | Fechner | A01N 59/16 428/409 |
| 2007/0195259 A1* | 8/2007 | Olsson | G02C 5/00 351/43 |

FOREIGN PATENT DOCUMENTS

CN          101812678 B   *  5/2012

* cited by examiner

*Primary Examiner* — Abigail Vanhorn
(74) *Attorney, Agent, or Firm* — ScienBiziP, P.C.

(57) ABSTRACT

An antibacterial spectacle part comprises a spectacle part, and a film formed on at least one surface of the spectacle part. The film is formed by a self-polymerization reaction of dopamine, and comprises a plurality of silver nano particles deposited on a surface of the film away from the spectacle part. The disclosure also provides an antibacterial treatment method.

8 Claims, 2 Drawing Sheets

ANTIBACTERIAL SPECTACLE PART AND ANTIBACTERIAL TREATMENT METHOD

FIELD

The subject matter herein generally relates to an antibacterial spectacle part and an antibacterial treatment method.

BACKGROUND

Contact lenses are commonly worn by users to correct vision, or for cosmetic or therapeutic reasons. Usually, a contact lens needs antibacterial agents disposed on the surface, to prevent a user from suffering from eye damage such as acute red eye or microbial keratitis.

BRIEF DESCRIPTION OF THE DRAWINGS

Implementations of the present technology will now be described, by way of example only, with reference to the attached figures.

DETAILED DESCRIPTION

Figure 1:
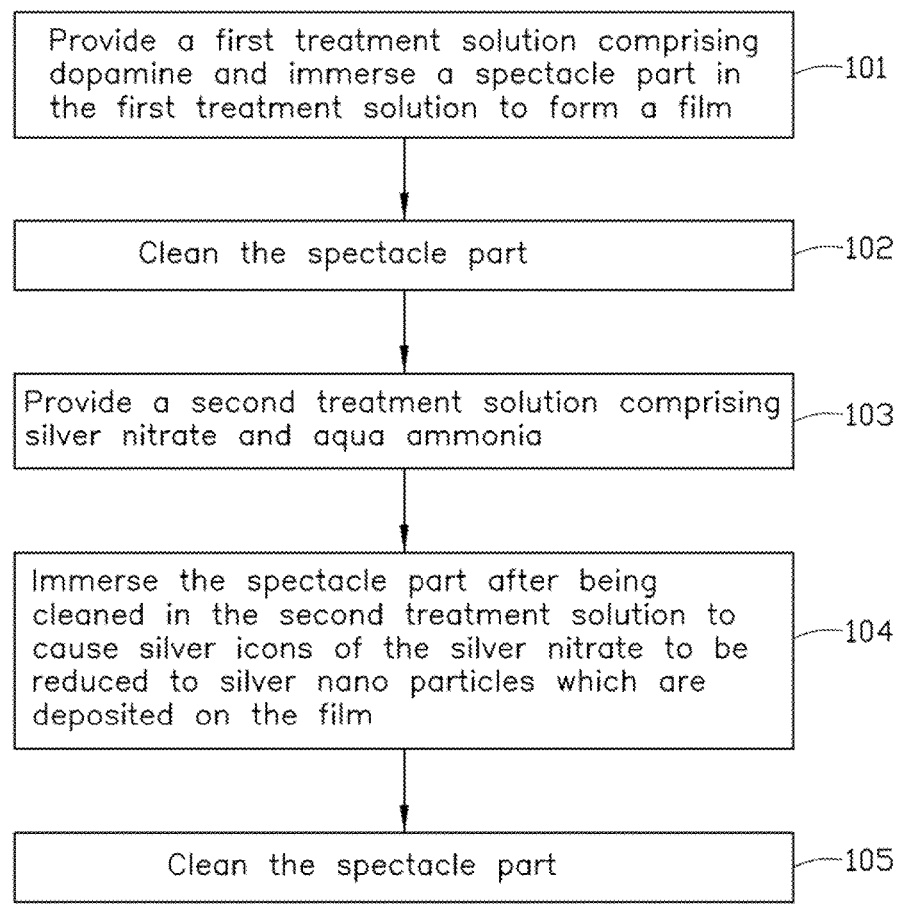
FIG. 1 is a flowchart of an exemplary embodiment of an antibacterial treatment method.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series and the like.

FIG. 1 illustrates a flowchart of an antibacterial treatment method in accordance with an exemplary embodiment. The exemplary method is provided by way of example, as there are a variety of ways to carry out the method. Each block shown in FIG. 1 represents one or more processes, methods, or subroutines, carried out in the exemplary method. Furthermore, the illustrated order of blocks is by example only and the order of the blocks can change. Additional blocks may be added or fewer blocks may be utilized, without departing from this disclosure. The exemplary method can begin at block 101.

At block 101, a first treatment solution is provided which comprises dopamine, inorganic oxide particles, and an alkaline solution. The spectacle part which needs antibacterial treatment is immersed in the first treatment solution for about 1 min to about 1 hour. Thus, when the dopamine undergoes a self-polymerization reaction in the alkaline solution to form a film, the film is bonded to a surface of the spectacle part by at least one of intermolecular force (such as hydrogen bonding) and covalent bonding (such as π-π bonding), and the inorganic oxide particles are dispersed in the film. The inorganic oxide particles are boned to the film by at least one of hydrogen bonding and π-π bonding. The dopamine has the chemical formula:

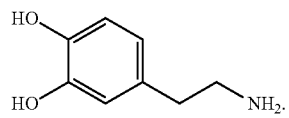 [SMILES: NCCc1ccc(O)c(O)c1]

In at least one exemplary embodiment, the spectacle part can be a contact lens, a spectacle frame, or a spectacle lens fixed on the spectacle frame. In the illustrated exemplary embodiment, the spectacle part is a contact lens.

In at least one exemplary embodiment, the film has a thickness of about 0.1 µm to about 50 µm.

The dopamine has a mass percentage of about 1% to about 40% of a total mass of the first treatment solution. The inorganic oxide particles have a mass percentage of about 9.5% to about 55% of the total mass of the first treatment solution. The alkaline solution has a mass percentage of about 6% to about 65% of the total mass of the first treatment solution. The dopamine is dissolved in the alkaline solution.

The inorganic oxide particles may be selected from a group consisting of silicon dioxide nano particles, zirconia nano particles, aluminum oxide nano particles, and titanium dioxide nano particles. Each inorganic oxide particle has a diameter of about 1 nm to about 1000 nm.

In another exemplary embodiment, the inorganic oxide particles can be omitted. The dopamine has a mass percentage of about 0.5% to about 94% of a total mass of the first treatment solution, and the alkaline solution has a mass percentage of about 6% to about 99.5% of the total mass of the first treatment solution.

The alkaline solution is formed by mixing ethyl alcohol, water, and aqua ammonia. The ethyl alcohol has a mass percentage of about 5% to about 35% of a total mass of the alkaline solution. The water has a mass percentage of about 42% to about 85% of the total mass of the alkaline solution. The aqua ammonia has a mass percentage of about 0.5% to about 24% of the total mass of the alkaline solution. In at least one exemplary embodiment, the ethyl alcohol, the water, and the aqua ammonia are in a ratio of 4:9:0.6 by volume.

In at least one exemplary embodiment, the aqua ammonia has a mass concentration of about 25% to about 28%.

At block 102, the spectacle part is taken out of the first treatment solution, and is cleaned to remove any unreacted first treatment solution on the spectacle part. In the illustrated exemplary embodiment, the spectacle part is immersed in water for about 30 sec to about 30 min to clean the spectacle part.

At block 103, a second treatment solution is provided which comprises silver nitrate and aqua ammonia.

The silver nitrate in the second treatment solution has a concentration of about 0.01 mol/L to about 0.2 mol/L. The aqua ammonia has a mass concentration of about 25% to about 28%.

At block 104, after being cleaned, the spectacle part is immersed in the second treatment solution for about 1 hour to about 48 hours, to cause the silver nitrate and catechol groups of the dopamine on a surface of the film away from the spectacle part to undergo a redox reaction. That is, silver ions of the silver nitrate are reduced to silver nano particles which are deposited on the surface of the film, to allow the spectacle part to have an antibacterial ability. The catechol groups of the dopamine on the surface of the film are oxidized to 1,2-benzoquinone groups.

At block 105, the spectacle part is taken out of the second treatment solution and is cleaned to any unreacted the second treatment solution on the spectacle part, thereby forming an antibacterial spectacle part. In the exemplary embodiment, the antibacterial spectacle part is immersed in water for about 30 sec to about 30 min to clean.

EXAMPLE 1

Aqua ammonia having a mass concentration of 25% was provided. An alkaline solution was formed by mixing ethyl alcohol, water, and aqua ammonia in a ratio of 4:9:0.6 by volume. A first treatment solution was formed by adding about 58 g of dopamine and about 42 g of silicon dioxide nano particles into about 100 g of the alkaline solution and stirring until the dopamine is dissolved in the alkaline solution. A spectacle part was immersed in the first treatment solution for 10 min and then in water for 10 min to clean. A second treatment solution was formed by dissolving silver nitrate in aqua ammonia. The aqua ammonia had a mass concentration of 25%. The silver nitrate had a concentration of 0.2 mol/L in the second treatment solution. The spectacle part after being cleaned was immersed in the second treatment solution for 24 hours and then in water for 10 min.

EXAMPLE 2

Aqua ammonia having a mass concentration of 28% was provided. An alkaline solution was formed by mixing ethyl alcohol, water, and aqua ammonia in a ratio of 3.5:10.2:0.65 by volume. A first treatment solution was formed by adding about 62 g of dopamine, about 9.6 g of silicon dioxide nano particles, and about 6.4 g of zirconia nano particles into about 83 g of the alkaline solution and stirring until the dopamine is dissolved in the alkaline solution. A spectacle part was immersed in the first treatment solution for 8 min and then in water for 10 min to clean. A second treatment solution was formed by dissolving silver nitrate in aqua ammonia. The aqua ammonia had a mass concentration of 25%. The silver nitrate had a concentration of 0.18 mol/L in the second treatment solution. The spectacle part after being cleaned was immersed in the second treatment solution for 48 hours and then in water for 10 min.

EXAMPLE 3

Aqua ammonia having a mass concentration of 28% was provided. An alkaline solution was formed by mixing ethyl alcohol, water, and aqua ammonia in a ratio of 1.8:10.2:0.3 by volume. A first treatment solution was formed by adding about 59.5 g of dopamine and about 39.8 g of titanium dioxide nano particles into about 120 g of the alkaline solution and stirring until the dopamine is dissolved in the alkaline solution. A spectacle part was immersed in the first treatment solution for 12 min, and then was water for 5 min to clean. A second treatment solution was formed by dissolving silver nitrate in aqua ammonia. The aqua ammonia had a mass concentration of 25%. The silver nitrate solution had a concentration of 0.15 mol/L in the second treatment. The spectacle part after being cleaned was immersed in the second treatment solution for 48 hours and then was water for 10 min.

EXAMPLE 4

Aqua ammonia having a mass concentration of 28% was provided. An alkaline solution was formed by mixing ethyl alcohol, water, and aqua ammonia in a ratio of 2.3:11:0.75 by volume. A first treatment solution was formed by adding about 35 g of dopamine, about 20 g of silicon dioxide nano particles, and about 8 g of titanium dioxide nano particles into about 79 g of the alkaline solution and stirring until the dopamine is dissolved in the alkaline solution. A spectacle part was immersed in the first treatment solution for 35 min and then in water for 10 min to clean. A second treatment solution was formed by dissolving silver nitrate in aqua ammonia. The aqua ammonia had a mass concentration of 25%. The silver nitrate had a concentration of 0.2 mol/L in the second treatment solution. The spectacle part after being cleaned was immersed in the second treatment solution for 30 hours and then in water for 20 min.

EXAMPLE 5

Aqua ammonia having a mass concentration of 25% was provided. An alkaline solution was formed by mixing ethyl alcohol, water, and aqua ammonia in a ratio of 4:9:0.6 by volume. A first treatment solution was formed by adding about 8 g of dopamine into about 100 g of the alkaline solution and stirring until the dopamine is dissolved in the alkaline solution. A spectacle part was immersed in the first treatment solution for 10 min and then was water for 10 min to clean. A second treatment solution was formed by dissolving silver nitrate in aqua ammonia. The aqua ammonia had a mass concentration of 25%. The silver nitrate had a concentration of 0.2 mol/L in the second treatment solution. The spectacle part after being cleaned was immersed in the second treatment solution for 24 hours and then was water for 10 min.

Figure 2:
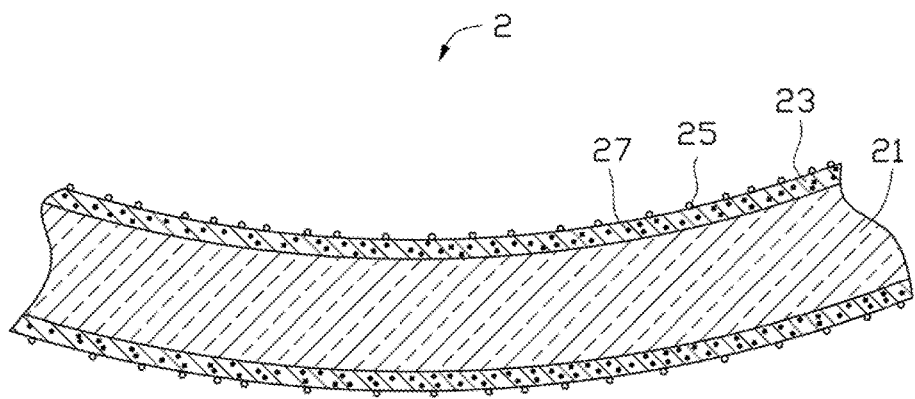
FIG. 2 is a cross-sectional view of an exemplary embodiment of a portion of an antibacterial spectacle part.

FIG. 2 illustrates an exemplary embodiment of an antibacterial spectacle part 2. The antibacterial spectacle part 2 comprises a spectacle part 21 and a film 23 formed on at least one surface of the spectacle part 21. The film 23 is formed by a self-polymerization reaction of dopamine, and comprises a plurality of silver nano particles 25 deposited on a surface of the film 23 away from the spectacle part 21. The spectacle part 21 may be a contact lens, a spectacle frame, or a spectacle lens fixed on the spectacle frame. In the illustrated exemplary embodiment, the spectacle part 21 is a contact lens.

In at least one exemplary embodiment, the film 23 can comprise a plurality of inorganic oxide particles 27 to enhance a hardness of the film 23. The inorganic oxide particles 27 are dispersed in the film 23.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:
1. An antibacterial treatment method comprising:
dissolving dopamine in an alkaline solution to form a first treatment solution and immersing a spectacle part in the first treatment solution, to cause the dopamine to undergo a self-polymerization reaction to form a film on at least one surface of the spectacle part; and immersing the spectacle part in a second treatment solution comprising silver nitrate and aqua ammonia, to cause the silver nitrate and catechol groups of the dopamine on a surface of the film away from the spectacle part to undergo a redox reaction, so that silver icons of the silver nitrate are reduced to silver nano particles which are deposited on the surface of the film;

wherein the film further comprises inorganic oxide particles selected from a group consisting of silicon dioxide nano particles, zirconia nano particles, and aluminum oxide nano particles, the alkaline solution is formed by mixing ethyl alcohol, water, and aqua ammonia.

2. The antibacterial treatment method of claim 1, wherein the dopamine has a mass percentage of 0.5% to 94% of a total mass of the first treatment solution, and the alkaline solution has a mass percentage of 6% to 99.5% of the total mass of the first treatment solution.

3. The antibacterial treatment method of claim 1, wherein the ethyl alcohol has a mass percentage of 5% to 35% of a total mass of the alkaline solution, the water has a mass percentage of 42% to 85% of the total mass of the alkaline solution, and the aqua ammonia has a mass percentage of 0.5% to 24% of the total mass of the alkaline solution.

4. The antibacterial treatment method of claim 3, wherein the aqua ammonia has a mass concentration of 25% to 28% in the second treatment solution.

5. The antibacterial treatment method of claim 1, wherein the silver nitrate has a concentration of 0.01 mol/L to 0.2 mol/L in the second treatment solution, and the aqua ammonia has a mass concentration of 25% to 28% in the second treatment solution.

6. The antibacterial treatment method of claim 1, wherein each inorganic oxide particle has a diameter of 1 nm to 1000 nm.

7. The antibacterial treatment method of claim 1, wherein the dopamine has a mass percentage of 1% to 40% of a total mass of the first treatment solution, the inorganic oxide particles have a mass percentage of 9.5% to 55% of the total mass of the first treatment solution, and the alkaline solution has a mass percentage of 6% to 65% of the total mass of the first treatment solution.

8. The antibacterial treatment method of claim 1, wherein the spectacle part is immersed in the first treatment solution for 1 min to 1 hour, the spectacle part is immersed in the second treatment solution for 1 min to 1 hour.

* * * * *